(12) United States Patent  
Thornton

(10) Patent No.: US 8,874,251 B2  
(45) Date of Patent: Oct. 28, 2014

(54) SYSTEM AND METHOD FOR FORMING A CUSTOM MEDICAL MASK FROM A THREE-DIMENSIONAL ELECTRONIC MODEL

(75) Inventor: W. Keith Thornton, Dallas, TX (US)

(73) Assignee: Airway Technologies, LLC, Carrollton, TX (US)

( * ) Notice: Subject to any disclaimer, the term of this patent is extended or adjusted under 35 U.S.C. 154(b) by 1803 days.

(21) Appl. No.: 11/768,457

(22) Filed: Jun. 26, 2007

(65) Prior Publication Data

US 2008/0006273 A1   Jan. 10, 2008

Related U.S. Application Data

(60) Provisional application No. 60/806,657, filed on Jul. 6, 2006.

(51) Int. Cl.
*G01F 19/00* (2006.01)
*A61F 2/50* (2006.01)
*A61M 16/06* (2006.01)

(52) U.S. Cl.
CPC ........... *A61M 16/06* (2013.01); *A61M 16/0683* (2013.01); *A61M 2016/0661* (2013.01)
USPC .. 700/118; 700/163; 128/206.21; 128/205.25

(58) Field of Classification Search
CPC ............ A61M 16/06; A61M 16/0683; A61M 2016/0661
USPC ................. 700/182, 163; 128/206.21, 205.25
See application file for complete search history.

(56) References Cited

U.S. PATENT DOCUMENTS

| 339,334 A | 4/1886 | Searle |
| 690,663 A | 1/1902 | Pratt |

(Continued)

FOREIGN PATENT DOCUMENTS

| DE | 156627 | 12/1904 | |
| DE | 2 320 501 | 11/1974 | ............... A61F 5/56 |

(Continued)

OTHER PUBLICATIONS

Kim et al, Offset of STL Model generated from Solid Model, Sep. 2005, Journal of the Korean Society of Precision engineering, vol. 22, No. 9, pp. 202-210.*

(Continued)

*Primary Examiner* — Kavita Padmanabhan
*Assistant Examiner* — Olvin Lopez Alvarez
(74) *Attorney, Agent, or Firm* — Baker Botts L.L.P.

(57) ABSTRACT

According to one embodiment, a custom medical mask formed for a particular user from a three-dimensional electronic model includes a body formed from a polymerized photopolymer material. An interior surface of the body is configured to seat on the particular user's face and comprises a physical embodiment of a three-dimensional electronic model corresponding to unique facial features of the particular user. According to another embodiment, a method of creating a three-dimensional electronic model for use in forming a custom medical mask for a particular user includes scanning a portion of the particular user's face using an electronic scanning device, generating a three-dimensional electronic model of the portion of the particular user's face based on the scanning, and transmitting the three-dimensional electronic model of the portion of the particular user's face for use in forming the custom medical mask for the particular user from a photopolymer using a stereolithography apparatus.

17 Claims, 6 Drawing Sheets

(56) References Cited

U.S. PATENT DOCUMENTS

| | | | |
|---|---|---|---|
| 746,869 A | 12/1903 | Moulton | |
| 774,446 A | 11/1904 | Moulton | |
| 781,516 A | 1/1905 | Guthrie, Jr. | |
| 885,196 A | 4/1908 | Steil | |
| 893,213 A | 7/1908 | Whiteway | |
| 955,562 A | 4/1910 | Thomas | |
| 996,783 A | 7/1911 | Moreau | |
| 1,076,534 A | 10/1913 | Wallen | |
| 1,146,264 A | 7/1915 | Kelly | |
| 1,483,694 A | 2/1924 | Stukey | |
| 1,592,345 A | 7/1926 | Drager | |
| 1,649,664 A | 11/1927 | Carter | |
| 1,674,336 A | 6/1928 | King | |
| 1,675,202 A | 6/1928 | Warne | |
| 1,679,748 A | 8/1928 | Stratton | |
| 2,171,695 A | 9/1939 | Harper | 32/19 |
| 2,178,128 A | 10/1939 | Waite | 128/136 |
| 2,383,649 A | 8/1945 | Heidbrink | 128/142 |
| 2,424,533 A | 7/1947 | Faires | 128/136 |
| 2,505,028 A | 4/1950 | Boeger | 128/215 |
| 2,521,039 A | 9/1950 | Carpenter | 128/136 |
| 2,521,084 A | 9/1950 | Oberto | 128/141 |
| 2,531,222 A | 11/1950 | Kesling | 32/14 |
| 2,574,623 A | 11/1951 | Clyde | 128/136 |
| 2,590,118 A | 3/1952 | Oddo, Jr. | 128/136 |
| 2,627,268 A | 2/1953 | Leppich | 128/136 |
| 2,671,446 A | 3/1954 | Mann | 128/163 |
| 2,712,160 A | 7/1955 | Sterczek | 18/55.05 |
| 2,833,278 A | 5/1958 | Ross | 128/136 |
| 2,867,212 A | 1/1959 | Nunn, Jr. | 128/136 |
| 2,882,893 A | 4/1959 | Godfroy | 128/136 |
| 2,917,045 A | 12/1959 | Schildknecht et al. | 128/141 |
| 2,977,636 A | 4/1961 | McGuire | 18/58.7 |
| 3,037,501 A | 6/1962 | Miller | 128/141 |
| 3,064,354 A | 11/1962 | Pos | 32/19 |
| 3,107,668 A | 10/1963 | Thompson | 128/136 |
| 3,124,129 A | 3/1964 | Grossberg | 128/136 |
| 3,132,647 A | 5/1964 | Corniello | 128/136 |
| 3,219,033 A | 11/1965 | Wallshein | 128/136 |
| 3,277,892 A | 10/1966 | Tepper | 128/172.1 |
| 3,312,216 A | 4/1967 | Wallshein | 128/136 |
| 3,321,832 A | 5/1967 | Weisberg | 32/32 |
| 3,330,274 A | 7/1967 | Bennett | 128/146.7 |
| 3,360,860 A | 1/1968 | Roland | 32/17 |
| 3,434,470 A | 3/1969 | Strickland | 128/136 |
| 3,457,916 A | 7/1969 | Wolicki | 128/136 |
| 3,513,838 A | 5/1970 | Foderick et al. | 128/136 |
| 3,522,805 A | 8/1970 | Wallshein | 128/136 |
| 3,658,058 A | 4/1972 | Neidhart et al. | 128/147 |
| 3,690,004 A | 9/1972 | Frush | 32/17 |
| 3,695,265 A | 10/1972 | Brevik | 128/146.2 |
| 3,845,768 A | 11/1974 | Garrahan | 128/142.7 |
| 3,854,208 A | 12/1974 | Arant | 32/19 |
| 3,864,832 A | 2/1975 | Carlson | 32/40 R |
| 3,871,370 A | 3/1975 | McDonald | 128/136 |
| 3,882,601 A | 5/1975 | Jahn | 32/17 |
| 3,884,226 A | 5/1975 | Tepper | 128/136 |
| 4,016,650 A | 4/1977 | Leusner et al. | 32/17 |
| 4,021,858 A * | 5/1977 | Neeld et al. | 2/9 |
| 4,026,024 A | 5/1977 | Tradowsky | 32/19 |
| 4,114,614 A | 9/1978 | Kesling | 128/136 |
| 4,169,473 A | 10/1979 | Samelson | 128/136 |
| 4,182,312 A | 1/1980 | Mushabac | 433/68 |
| 4,227,877 A | 10/1980 | Tureaud et al. | 433/37 |
| 4,233,972 A | 11/1980 | Hauff et al. | 128/205.12 |
| 4,289,127 A | 9/1981 | Nelson | 128/207.14 |
| 4,294,243 A | 10/1981 | Ernsting et al. | 128/201.18 |
| 4,304,227 A | 12/1981 | Samelson | 128/136 |
| 4,345,592 A | 8/1982 | Giorgini et al. | 128/204.26 |
| 4,345,593 A | 8/1982 | Sullivan | 128/204.26 |
| 4,376,628 A | 3/1983 | Aardse | 433/80 |
| 4,382,783 A | 5/1983 | Rosenberg | 433/19 |
| 4,392,490 A | 7/1983 | Mattingly et al. | 128/202.27 |
| 4,397,701 A | 8/1983 | Johnson et al. | 156/62 |
| 4,433,956 A | 2/1984 | Witzig | 433/7 |
| 4,439,147 A | 3/1984 | Magill et al. | 433/3 |
| 4,439,149 A | 3/1984 | Devincenzo | 433/6 |
| 4,454,090 A | 6/1984 | Saumell | 264/154 |
| 4,470,413 A | 9/1984 | Warncke | 128/201.18 |
| 4,495,945 A | 1/1985 | Liegner | 128/200.26 |
| 4,505,672 A | 3/1985 | Kurz | 433/6 |
| 4,530,662 A | 7/1985 | Andersson et al. | 433/37 |
| 4,553,549 A | 11/1985 | Pope et al. | 128/421 |
| 4,568,280 A | 2/1986 | Ahlin | 433/6 |
| 4,569,342 A | 2/1986 | von Nostitz | 128/136 |
| 4,575,330 A * | 3/1986 | Hull | 425/174.4 |
| 4,593,686 A | 6/1986 | Lloyd et al. | 128/136 |
| 4,602,905 A | 7/1986 | O'Keefe, III | 433/41 |
| 4,639,220 A | 1/1987 | Nara et al. | 433/69 |
| 4,655,213 A | 4/1987 | Rapoport et al. | 128/205.25 |
| 4,668,188 A | 5/1987 | Wolfenson et al. | 433/37 |
| 4,669,459 A | 6/1987 | Spiewak et al. | 128/136 |
| 4,676,240 A | 6/1987 | Gardy | 128/207.14 |
| 4,706,683 A | 11/1987 | Chilton et al. | 128/654 |
| 4,715,368 A | 12/1987 | George | 128/136 |
| 4,773,853 A | 9/1988 | Kussick | 433/6 |
| 4,784,123 A | 11/1988 | Robeson | 128/90 |
| 4,799,500 A | 1/1989 | Newbury | 128/859 |
| 4,858,605 A | 8/1989 | Levy | |
| 4,858,606 A | 8/1989 | Hamlin | 128/204.29 |
| 4,862,903 A | 9/1989 | Campbell | 128/861 |
| 4,870,962 A | 10/1989 | Sitnik | 128/205.13 |
| 4,886,056 A | 12/1989 | Simpson | 128/201.25 |
| 4,892,478 A | 1/1990 | Tateosian et al. | 433/6 |
| 4,901,737 A | 2/1990 | Toone | 128/848 |
| 4,906,234 A | 3/1990 | Voychehovski | 604/79 |
| 4,919,128 A | 4/1990 | Kopala et al. | 128/207.18 |
| 4,932,867 A | 6/1990 | Ueno | 433/69 |
| 4,941,212 A | 7/1990 | Liff | 2/206 |
| 4,955,393 A | 9/1990 | Adell | 128/859 |
| RE33,442 E | 11/1990 | George | 128/860 |
| 5,003,994 A | 4/1991 | Cook | 128/848 |
| 5,011,407 A | 4/1991 | Pelerin | 433/48 |
| 5,018,533 A | 5/1991 | Hawkins | 128/848 |
| 5,026,278 A | 6/1991 | Oxman et al. | 433/41 |
| 5,028,232 A | 7/1991 | Snow | 433/24 |
| 5,040,976 A | 8/1991 | Ubel, III et al. | 433/41 |
| 5,042,478 A | 8/1991 | Kopala et al. | 128/207.18 |
| 5,042,506 A | 8/1991 | Liberati | 128/848 |
| 5,046,512 A | 9/1991 | Murchie | 128/848 |
| 5,052,409 A | 10/1991 | Tepper | 128/859 |
| 5,055,039 A | 10/1991 | Abbatte et al. | 433/24 |
| 5,056,534 A | 10/1991 | Wright | 128/848 |
| 5,062,421 A | 11/1991 | Burns et al. | 128/205.27 |
| 5,064,371 A | 11/1991 | Smeltzer | 433/37 |
| 5,065,756 A | 11/1991 | Rapoport | 128/204.18 |
| 5,066,231 A | 11/1991 | Oxman et al. | 433/214 |
| 5,078,600 A | 1/1992 | Austin | 433/73 |
| 5,092,346 A | 3/1992 | Hays et al. | 128/848 |
| 5,103,838 A | 4/1992 | Yousif | 128/859 |
| 5,112,225 A | 5/1992 | Diesso | 433/48 |
| 5,117,816 A | 6/1992 | Shapiro et al. | 128/200.24 |
| 5,154,184 A | 10/1992 | Alvarez | 128/848 |
| 5,154,609 A | 10/1992 | George | 433/68 |
| 5,183,057 A | 2/1993 | Syrop et al. | 128/845 |
| 5,188,529 A | 2/1993 | Lüth | 433/68 |
| 5,190,457 A | 3/1993 | Schreinemakers | 433/214 |
| 5,193,532 A | 3/1993 | Moa et al. | 128/204.25 |
| 5,213,498 A | 5/1993 | Pelerin | 433/37 |
| 5,233,978 A | 8/1993 | Callaway | 128/205.25 |
| 5,243,971 A | 9/1993 | Sullivan et al. | 128/205.25 |
| 5,245,995 A | 9/1993 | Sullivan et al. | 128/204.23 |
| 5,267,557 A | 12/1993 | Her-Mou | 128/206.21 |
| 5,267,862 A | 12/1993 | Parker | 433/215 |
| 5,277,202 A | 1/1994 | Hays | 128/848 |
| 5,284,161 A | 2/1994 | Karell | 128/848 |
| 5,313,960 A | 5/1994 | Tomasi | 128/848 |
| 5,316,020 A | 5/1994 | Truffer | 128/848 |
| 5,320,533 A | 6/1994 | Lee | 433/218 |
| 5,365,945 A | 11/1994 | Halstrom | 128/848 |
| 5,370,533 A | 12/1994 | Bushnell | 433/36 |
| 5,373,859 A | 12/1994 | Forney | 128/846 |
| 5,392,773 A | 2/1995 | Bertrand | 128/206.11 |
| 5,409,017 A | 4/1995 | Lowe | 128/848 |

(56) References Cited

U.S. PATENT DOCUMENTS

| | | | |
|---|---|---|---|
| 5,415,544 A | 5/1995 | Oxman et al. | 433/48 |
| 5,427,117 A | 6/1995 | Thornton | 128/848 |
| 5,456,264 A | 10/1995 | Series et al. | 128/725 |
| 5,458,137 A | 10/1995 | Axe et al. | 128/204.23 |
| 5,477,850 A | 12/1995 | Zegler et al. | 128/202.11 |
| 5,503,146 A | 4/1996 | Froehlich et al. | 128/204.23 |
| 5,503,552 A | 4/1996 | Diesso | 433/37 |
| 5,517,983 A | 5/1996 | Deighan et al. | 128/204.23 |
| 5,537,994 A | 7/1996 | Thornton | 128/204.18 |
| 5,537,999 A | 7/1996 | Dearman et al. | 128/205.25 |
| 5,538,000 A | 7/1996 | Rudolph | 128/205.25 |
| 5,538,014 A | 7/1996 | Wilson et al. | 128/863 |
| 5,540,223 A | 7/1996 | Starr et al. | 128/205.25 |
| 5,551,419 A | 9/1996 | Froehlich et al. | 128/204.23 |
| 5,551,872 A | 9/1996 | Mena | 433/37 |
| 5,558,090 A | 9/1996 | James | 128/207.18 |
| RE35,339 E | 10/1996 | Rapoport | 128/204.18 |
| 5,560,354 A | 10/1996 | Berthon-Jones et al. | 128/205.25 |
| 5,562,449 A | 10/1996 | Jacobs et al. | 433/215 |
| 5,566,683 A | 10/1996 | Thornton | 128/848 |
| 5,582,517 A | 12/1996 | Adell | 433/6 |
| 5,592,935 A | 1/1997 | Elstran et al. | 128/205.29 |
| 5,611,485 A | 3/1997 | Davis | 239/8 |
| 5,657,751 A | 8/1997 | Karr, Jr. | 128/205.18 |
| 5,657,752 A | 8/1997 | Landis et al. | 128/207.13 |
| 5,662,101 A | 9/1997 | Ogden et al. | 128/205.25 |
| 5,676,133 A | 10/1997 | Hickle et al. | 128/205.12 |
| 5,678,567 A | 10/1997 | Thornton et al. | 128/848 |
| 5,681,164 A | 10/1997 | Bass | 433/6 |
| 5,687,715 A | 11/1997 | Landis et al. | 128/207.18 |
| 5,713,349 A | 2/1998 | Keaney | 128/204.23 |
| 5,718,244 A | 2/1998 | Thornton | 128/864 |
| 5,718,500 A | 2/1998 | Vinci guerra et al. | 2/431 |
| 5,720,280 A | 2/1998 | Elstran et al. | 128/205.25 |
| 5,720,302 A | 2/1998 | Belfer | 128/848 |
| 5,724,965 A | 3/1998 | Handke et al. | 128/207.13 |
| 5,746,201 A | 5/1998 | Kidd | 128/206.24 |
| 5,752,510 A | 5/1998 | Goldstein | 128/207.18 |
| 5,755,219 A | 5/1998 | Thornton | 128/201.18 |
| 5,807,100 A | 9/1998 | Thornton | 433/48 |
| 5,810,749 A | 9/1998 | Maas | 602/6 |
| 5,829,441 A | 11/1998 | Kidd et al. | 128/848 |
| 5,832,918 A | 11/1998 | Pantino | 128/205.25 |
| 5,846,082 A | 12/1998 | Thornton | 433/215 |
| 5,887,587 A | 3/1999 | Groenke | 128/207.13 |
| 5,891,372 A | 4/1999 | Besset et al. | 264/46.5 |
| 5,954,048 A | 9/1999 | Thornton | 128/201.18 |
| 5,983,892 A | 11/1999 | Thornton | 128/201.26 |
| 5,988,166 A | 11/1999 | Hayek | 128/205.26 |
| 6,012,455 A | 1/2000 | Goldstein | 128/207.18 |
| 6,083,442 A | 7/2000 | Gabilly | 264/163 |
| 6,109,265 A | 8/2000 | Frantz et al. | 128/848 |
| 6,119,694 A | 9/2000 | Correa et al. | 128/207.13 |
| 6,123,071 A | 9/2000 | Berthon-Jones et al. | 128/204.18 |
| 6,155,262 A | 12/2000 | Thornton et al. | 128/859 |
| 6,209,542 B1 | 4/2001 | Thornton | 128/206.29 |
| 6,247,926 B1 | 6/2001 | Thornton | 433/48 |
| 6,263,871 B1 | 7/2001 | Brown et al. | 128/200.29 |
| D448,473 S | 9/2001 | Barnett et al. | D24/110.1 |
| 6,305,376 B1 | 10/2001 | Thornton | 128/848 |
| 6,318,997 B1 | 11/2001 | Mayweather | 433/45 |
| 6,325,064 B1 | 12/2001 | Thornton | 128/204.18 |
| 6,374,824 B1 | 4/2002 | Thornton | 128/201.26 |
| 6,405,729 B1 | 6/2002 | Thornton | 128/848 |
| 6,406,658 B1* | 6/2002 | Manners et al. | 264/401 |
| 6,412,488 B1 | 7/2002 | Barnett et al. | 128/207.13 |
| 6,464,924 B1 | 10/2002 | Thornton | 264/331.12 |
| 6,494,206 B1 | 12/2002 | Bergamaschi et al. | 128/206.24 |
| 6,516,805 B1 | 2/2003 | Thornton | 128/848 |
| 6,571,798 B1 | 6/2003 | Thornton | 128/206.21 |
| 6,645,413 B2 | 11/2003 | Jacobs | 264/222 |
| 6,675,802 B1 | 1/2004 | Thornton | 128/206.29 |
| 6,845,774 B2 | 1/2005 | Gaskell | 128/848 |
| 6,857,428 B2 | 2/2005 | Thornton | |
| 6,877,513 B2 | 4/2005 | Scarberry et al. | 128/848 |
| 7,077,138 B2 | 7/2006 | Bateman et al. | 128/206.14 |
| 7,174,895 B2 | 2/2007 | Thornton et al. | 128/848 |
| 7,597,103 B2 | 10/2009 | Thornton et al. | |
| 2002/0000230 A1 | 1/2002 | Gaskell | |
| 2002/0129818 A1 | 9/2002 | Morgan et al. | |
| 2002/0185134 A1* | 12/2002 | Bishop | 128/206.25 |
| 2003/0217753 A1 | 11/2003 | Thornton | |
| 2004/0079730 A1* | 4/2004 | Ahrens et al. | 216/87 |
| 2004/0157527 A1* | 8/2004 | Omar | 446/268 |
| 2004/0237965 A1 | 12/2004 | Bibi et al. | 128/206.29 |
| 2004/0263863 A1* | 12/2004 | Rogers et al. | 356/602 |
| 2005/0016544 A1 | 1/2005 | Thornton | 128/207.18 |
| 2005/0150496 A1* | 7/2005 | Smaldone | 128/206.21 |
| 2006/0005837 A1 | 1/2006 | Thornton | 128/205.25 |
| 2006/0023228 A1* | 2/2006 | Geng | 356/601 |
| 2006/0124131 A1 | 6/2006 | Chandran et al. | 128/206.28 |
| 2007/0006879 A1 | 1/2007 | Thornton | |
| 2007/0125388 A1 | 6/2007 | Thornton | 128/848 |
| 2008/0006274 A1 | 1/2008 | Thornton | 128/206.21 |
| 2008/0032256 A1 | 2/2008 | Thornton | 433/57 |
| 2008/0060648 A1 | 3/2008 | Thornton et al. | |
| 2008/0078396 A1 | 4/2008 | Janbakhsh | 128/205.25 |

FOREIGN PATENT DOCUMENTS

| | | | | |
|---|---|---|---|---|
| EP | 0 312 368 | A1 | 4/1989 | A61F 5/56 |
| EP | 0 359 135 | A1 | 3/1990 | A63B 71/10 |
| FR | 2731624 | | 9/1996 | A61M 16/06 |
| GB | 1 569 129 | | 6/1980 | A61F 5/56 |
| GB | 2 072 567 | A | 10/1981 | B29D 31/00 |
| WO | WO 91/12777 | | 9/1991 | A61C 9/00 |
| WO | WO 97/25010 | | 7/1997 | |
| WO | WO 98/20924 | | 5/1998 | A61M 15/08 |
| WO | WO 98/26736 | | 6/1998 | A61F 5/56 |
| WO | WO 98/46177 | | 10/1998 | A61F 5/56 |

OTHER PUBLICATIONS

"The Logical Mask" http://sleepapneamasks.com.au/, 2002.*
Whitestone et al, "Fabrication of Total contact Burn Masks using Non-Contact Surface Scanning: A New Standard of Care", 1997, p. 1-8.*
Boedkeeper., "Stereolithography SLA for rapid Precision Prototypes", Jun. 13, 2006http://web.archive.org/web/20060613025216/http://boedeker.com/sla.htm, pp. 1-4.*
Wikipedia, "thermoplastic", 2011, pp. 13.*
Han et al, "Development of Prototypes of Half-Mask Facepieces for Koreans Using the 3D Digitizing Design Method: A Pilot Study", Oct. 27, 2004, pp. 1-10.*
Piccione et al, "Modeling the Interface Between a Respirator and the Human Face", Mar. 15, 1997, pp. 51.*
Amirav et al, "Design of Aerosol Face Masks for Children Using Computerized 3D Face Analysis", Jul. 2013, pp. 1-7.*
Ping Fu; Geomagic, *Mass Customization: A Revolution in the Making*; Geomagic, Inc.; http://www.geomagic.com/en/about_us/media/articles/revolution.php; 5 pages, Printed on Mar. 22, 2006.
Geomagic, Geomagic Dental, *Custom Digital Dental Software & Services*; Geomagic, Inc.; http://www.geomagic.com/en/products/dental; 1 page, Printed on Jun. 8, 2006.
Geomagic, *Dentistry Enters 3D Digital World*; Geomagic, Inc.; http://www.geomagic.com/en/solutions/kavo.php; 6 pages, Printed on Mar. 22, 2006.
Geomagic, *Invisible Braces: The Orthodontics Industry Goes Wireless*; Geomagic, Inc.; http://www.geomagic.com/en/solutions/invisalign.php; 2 pages, Printed on Mar. 22, 2006.
Geomagic,*Digital Duplication Helps Atlantis Components Deliver Pearly Whites to Mainstream Dentists*; Geomagic, Inc.; http://www.geomagic.com/en/solutions/atlantis.php; 4 pages, Printed on Mar. 22, 2006.
Mary Hanson; Applications, *Something to Smile About: 3D Graphics are Revolutionizing Oral Health Care*; 0272-1716/01/$10.00 © 2001 IEEE; pp. 14-20, Jul. 2001.
Geomagic, *Ormco's Custom-Design Process Puts Orthodontics on the Fast Track*; Geomagic, Inc.; http://www.geomagic.com/en/solutions/ormco.php; 6 pages, Printed on Mar. 22, 2006.

(56) References Cited

OTHER PUBLICATIONS

Geomagic, *Geomagic Helps GN ReSound Bring Hearing Aid Manufacturing Into the Digital Age With DSSP*; Geomagic, Inc.; http://www.geomagic.com/en/solutions/gnresound.php, 6 pages, Printed on Mar. 22, 2006.
Geomagic, Health Care, *Medical Reconstruction and Devices*; Geomagic, Inc.; http://www.geomagic.com/en/solutions/industry/medical_desc.php; 1 page, Printed on Mar. 22, 2006.
Geomagic, *University of Florida Nasal Cavity Model to Aid Fight Against Serious Nose Bleeds*, Geomagic, Inc.; http://www.geomagic.com/en/solutions/flonase.php; 2 pages, Printed on Mar. 22, 2006.
Geomagic, *Geomagic Receives U.S. Patent for Automatic Surfacing From Scan Data*; Geomagic, Inc.; http://www.geomagic.com/en/about_us/media/press_release/PR060215.php; 1 page, Printed on Mar. 22, 2006.
Geomagic, *New MobileScan3D Plugin for Geomagic Software Speeds Digital Reconstruction and Quality Inspection*; Geomagic, Inc.; http://www.geomagic.com/en/about_us/media/press_releases/PR060222.php; 2 pages, Printed on Mar. 22, 2006.
*Raindrop Geomagic, Genex Technologies to Provide 3D Photography Solutions for Mass Customization*; http://www10.mcadcafe.com/nbc/articles/view_article.php?section=CorpNews&article-id= . . . ; 2 pages, Printed on Mar. 22, 2006.
Leslie Versweyveld; Virtual Medical Worlds Monthly, *Raindrop Geomagic's 3D Models Make Invisalign Orthodontic System Fit for Mass Customisation*; http://www.hoise.com/vmw/01/articles/vmw/LV-VM-03-01-17.html; 2 pages, Printed on Mar. 22, 2006.
Kathleen Schalch; npr, *Ping Fu: Recreating the World in All Its Dimensions*; http://www.npr.org/templates/story/story.php?story-Id=5279787; 2 pages, Mar. 22, 2006.
Geomagic Press Release, *Geomagic Hits Record Revenue and Profit*; Geomagic, Inc.; http://www.geomagic.com/en/about_us/media/press_releases/PR060301.php; 2 pages, Mar. 1, 2006.
John Brant; Inc. Magazine, *Entrepreneur of the Year: The Dimensions of Ping Fu*; http://pf.inc.com/magazine/20051201/ping-fu.html; 13 pages, Dec. 2005.
Geomagic; Custom Manufacturing; *Mass Customization Manufacturing*; Geomagic, Inc.; http://www.geomagic.com/en/solutions/applications/manufacturing_desc.php; 1 page, Printed on Mar. 22, 2006.
Raindrop Geomagic; *Geomagic Studio 8*; End-to-End, Quick Start Guide; Raindrop Geomagic, Inc.; http://www.geomagic.com; 30 pages, Jan. 28, 2005.
Peter Marks; SME Blue Book Series 2005; *Capturing a Competitive Edge Through Digital Shape Sampling & Processing (DSSP)*; Published by the Society of Manufacturing Engineers; 28 pages, 2005.
Geomagic; *Measurement Systems (3D Scanner) Manufacturers*; 3D Scanners http://www.geomagic.com/en/dssp_resources/scanners/index.php; 2 pages, 2006.
Yahoo! Finance Press Release; *Creaform Combines Handyscan 3D & Geomagic to Provide Real-Time Processing and Graphics*; http://biz.yahoo.com/bw/060103/20060103005371.html?.v=1&printer=1; 2 pages, Jan. 3, 2006.
Inition; *Polhemus FastScan Cobra/Scorpion—Handheld 3D Laser Scanners*; http://www.inition.co.uk/initiion/product.php?URL_=product_digiscan_polhemus_fastscan . . . ; 8 pages, Printed Mar. 22, 2006.
Peter Marks; Raindrop Geomagic; *3D Photography: A Catalyst for Billion-Dollar Industries*; 5 pages, Printed on Mar. 22, 2006.
Mayo Clinic Health Letter; Reliable Information for a Healthier Life; *Snoring: Laser Surgery Joins Battle to Restore Peace and Quiet*; vol. 13, No. 7, 8 pages, Jul. 1995.

Schmidt-Nowara, et al.; An American Sleep Disorders Association Review; *Oral Appliances for the Treatment of Snoring and Obstructive Sleep Apnea: A Review*; pp. 501-510, 1995.
CPAP-PRO—Introducing a New Comfort Level for CPAP Users brochure, 2 pages.
W. Keith Thornton, "Multi-Chamber Mask and Method of Forming the Same," pending U.S. Appl. No. 11/428,933, filed Jul. 6, 2006.
W. Keith Thornton, "Stability Medical Mask," pending U.S. Appl. No. 11/853,343, filed Sep. 11, 2007.
W. Keith Thornton, "System and Method for Custom-Orientihng a Medical Mask to an Oral Appliance," pending U.S. Appl. No. 11/947,291, filed Nov. 29, 2007.
PCT, Notification of Transmittal of the International Search Report and the Written Opinion of the International Searching Authority, or the Declaration, PCT/US06/26622, 11 pages, Date Mailed Feb. 21, 2007.
Photocopies of 2-piece dental device manufactured by Currie-Gibson Dental Laboratory, Inc., prior to Apr. 13, 1993, 5 pages.
Farrar, et al, *A Clinical Outline of Temporomandibular Joint Diagnosis and Treatment*, Normandie Study Group for TMJ Dysfunction, 3 pages, 1983.
Professional Positioners; *Dedicated to Excellence* brochure, 3 pages.
Great Lakes Orthodontics, Ltd.; *Nocturnal Airway Patency Appliance*; 2 pages.
George, Peter; *Treatment of Snoring and Obstructive Sleep Apnea with a Dental Device*; 5 pages, Jul.-Aug. 1993.
Database WOI, Section PQ, Week 9039, Derwent Publications, Ltd., London, GB; XP-002116355 Abstract—*Surgical Mouth Air Duct*; 1 page, Dec. 15, 1989.
"Donning the Mask," Dräger: X-plore 5500.2006.Dräger Safety, http://www.draeger-usa.com/ST/internet/pdf/US/protection/AnlegiPO_X-plore_5500_US.pdf, 2 pages, Accessed Sep. 14, 2006.
PCT Notification of Transmittal of the International Search Report or the Declaration for International Application No. PCT/US97/08708, 4 pages, Aug. 12, 1997.
PCT Invitation to Pay Additional Fees for International Application No. PCT/US03/13705, 6 pages, Oct. 10, 2003.
PCT Notification of Transmittal of the International Search Report and the Written Opinion of the International Searching Authority, or the Declaration, PCT/US 06/26622, 10 pages Mailing Date, Feb. 21, 2007.
Thornton, "Oral Appliance for Treating a Breathing Condition," pending U.S. Appl. No. 11/278,918, 42 pages, filed Apr. 6, 2006.
Park, Richard; "Dreaming Up New Products;" HomeCare; http://www.homecaremag.com/mag/medical_dreaming_new_products; 3 pages, Apr. 1, 2001.
B. Sanghera, et al.; "Preliminary study of potential for rapid prototype and surface scanned radiotherapy facemask production technique;" Journal of Medical Engineering & Technology; vol. 26; No. 1; pp. 16-21, Jan./Feb. 2002.
European Patent Office Communication, Application No. 03 809 555.0-1257, Applicant: W. Keith Thornton, 4 pages, dated Aug. 7, 2009.
PCT International Search Report, International Application No. PCT/US07/02736, 10 pages, Oct. 26, 2007.
Japanese Patent Office, Action Regarding Japanese Application No. 2004/500750, 4 pages, Oct. 14, 2008.
Canadian Intellectual Property Office, Application No. 2,502,280, Applicant: W. Keith Thornton, 3 pages, dated Feb. 23, 2010.

\* cited by examiner

SYSTEM AND METHOD FOR FORMING A CUSTOM MEDICAL MASK FROM A THREE-DIMENSIONAL ELECTRONIC MODEL

RELATED APPLICATION

This application claims the benefit under 35 U.S.C. §119(e) of U.S. Provisional Application Ser. No. 60/806,657 filed Jul. 6, 2006.

TECHNICAL FIELD

This invention relates generally to masks for use in medical and other clinical applications, and more particularly to a system and method for forming a custom medical mask from a three-dimensional electronic model.

BACKGROUND

Many people experience breathing problems on a recurring basis, which often result in sleep disordered breathing (i.e., difficulty sleeping, snoring, or other more serious conditions such as obstructive sleep apnea). As technology advances, people with such breathing problems demand increased performance and comfort. Previous devices for improving a user's breathing have included face masks, nose masks, or nasal inserts that help deliver air to the user's nose at positive pressure. These devices help force open the user's breathing passage and thereby improve the user's breathing. However, previous devices have often provided an inadequate fit and thus have caused discomfort for users and failed to adequately prevent leakage.

OVERVIEW

According to one embodiment, a custom medical mask formed for a particular user from a three-dimensional electronic model includes a body formed from a polymerized photopolymer material. An interior surface of the body is configured to seat on the particular user's face and comprises a physical embodiment of a three-dimensional electronic model corresponding to unique facial features of the particular user.

According to another embodiment, a method of creating a three-dimensional electronic model for use in forming a custom medical mask for a particular user includes scanning at least a portion of the particular user's face using an electronic scanning device, generating a three-dimensional electronic model of the portion of the particular user's face based on the scanning, and transmitting the three-dimensional electronic model of the portion of the particular user's face for use in forming the custom medical mask for the particular user from a photopolymer using a stereolithography apparatus.

According to another embodiment, a system for forming a custom medical mask for a particular user from a three-dimensional electronic model includes a photopolymer material, a three-dimensional electronic model of a custom medical mask, and a stereolithography apparatus. The three-dimensional electronic model includes a first surface that corresponds to unique facial features of the particular user. The stereolithography apparatus is operable to focus a light source on the photopolymer material in a pattern corresponding to the three-dimensional electronic model to polymerize the photopolymer material to form the custom medical mask for the particular user.

Certain embodiments may provide one or more technical advantages. For example, certain embodiments may provide a custom medical mask that conforms substantially optimally to a user's unique facial features. Certain embodiments may provide improved fit, increased comfort, reduced leakage, and improved performance, whether for treating sleep disordered breathing, administering anesthesia, or any other suitable purpose for which the custom medical mask is used. In certain embodiments the process of creating the three-dimensional electronic model does not apply any force to the particular user's face that may affect the shape of the model and the resulting custom medical mask. Certain embodiments may allow for the more efficient fabrication of a custom medical mask, which may include more efficient methods for fabricating one or more fittings and or openings for a custom medical mask. Certain embodiments may allow for data communication over the Internet or other network such that acquiring data needed to create the three-dimensional electronic model and fabricating the custom medical mask from the three-dimensional electronic model may be performed in different locations remote from one another. Certain embodiments may provide all, some, or none of these advantages. Certain embodiments may provide one or more other technical advantages, one or more of which may be apparent to those skilled in the art from the figures, descriptions, and claims included herein.

BRIEF DESCRIPTION OF THE DRAWINGS

For a more complete understanding of the present invention and certain of its advantages, reference is now made to the following description, taken in conjunction with the accompanying drawings, in which:

FIGS. 4A to 7 illustrate example electronic models for use in forming a custom medical mask;

FIG. 5 illustrates an example custom medical mask;

FIG. 7 illustrates an example custom medical mask with an oral chamber;

DESCRIPTION OF EXAMPLE EMBODIMENTS

Figure 1:
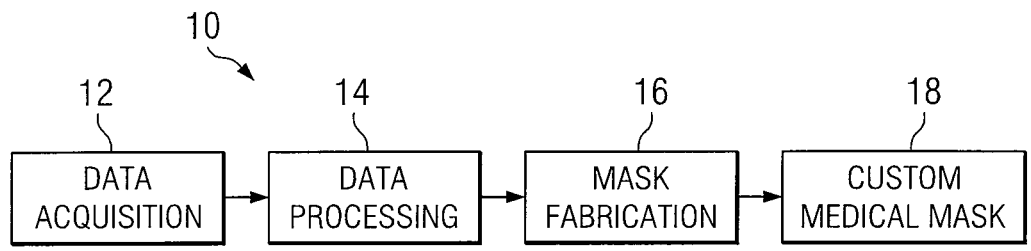
FIG. 1 illustrates an example method for forming a custom medical mask.

FIG. 1 illustrates an example method 10 for forming a custom medical mask 18. In certain embodiments, steps of method 10 may include data acquisition 12, data processing 14, and mask fabrication 16 to form custom medical mask 18.

In certain embodiments, data acquisition 12 may represent a process for collecting three-dimensional coordinate data corresponding to unique facial features of a particular user. In certain embodiments, data acquisition 12 may be performed using surface digitization and/or three-dimensional measurement techniques. For example, data acquisition 12 may utilize optical, acoustical, and/or other scanning techniques, physical probing techniques, and/or any other suitable techniques. In a particular embodiment, data acquisition 12 may utilize one or more optical scanners to acquire three-dimensional coordinate data corresponding to certain features of a particular user's face. The three-dimensional coordinate data collected through data acquisition 12 may be formatted in any suitable manner. For example, the three-dimensional coordinate data may be formatted as a three-dimensional computer aided drafting (CAD) model. In a particular embodiment, the three-dimensional coordinate data may be stored as one or more point-cloud models.

In certain embodiments, data processing 14 may represent one or more processes for electronically manipulating and/or modifying the coordinate data collected in data acquisition 12. These processes may include screening the coordinate data collected in data acquisition 12, fitting the coordinate data collected in data acquisition 12, converting the coordinate data collected in data acquisition 12 from one format to another, and/or any of a number of well-known data processing techniques known for use with three-dimensional coordinate data. For example, screening the coordinate data (also known as smoothing) may include identification, modification, and/or removal of outlier coordinate data points. As another example, fitting (also known as stitching) may include aligning multiple sets of coordinate data collected in data acquisition 12 such that the multiple sets may be used together to form a single coordinate data set. As another example, the coordinate data collected in data acquisition 12 may be formatted as a point-cloud model and may be converted to a polygon mesh model, Non-Uniform Rational B-Spline (NURBS) model, stereolithography (STL) model, and/or any other appropriate three-dimensional electronic model.

In certain embodiments, mask fabrication 16 may represent a process for forming custom medical mask 18 as a physical embodiment of a three-dimensional electronic model developed through data acquisition 12 and data processing 14. In particular embodiments, mask fabrication 16 may represent one or more well-known rapid-prototyping techniques such as, for example, three-dimensional printing (3DP), selective laser sintering (SLS), and/or STL. One or more of these processes may be used to form custom medical mask 18 as a physical embodiment of a three-dimensional electronic model, such that custom medical mask 18 is configured to provide a custom fit to unique facial features of a particular user.

Figure 2:
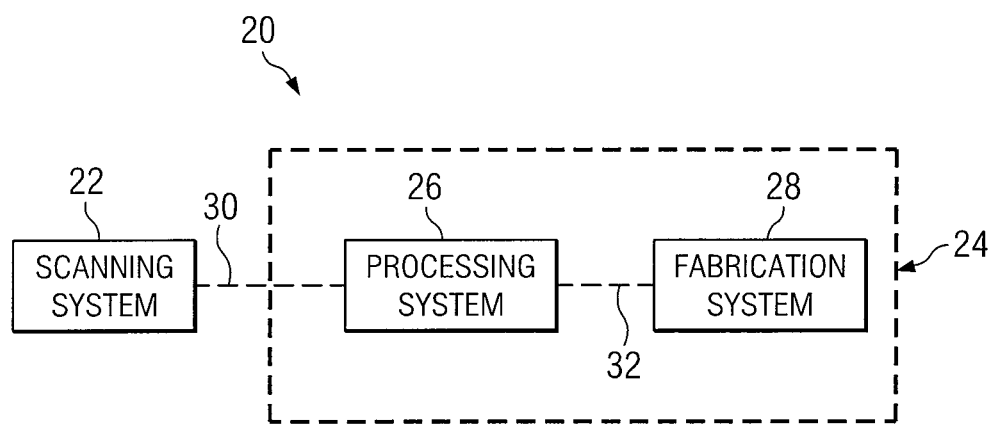
FIG. 2 illustrates an example system for forming a custom medical mask.

FIG. 2 illustrates an example system 20 for forming a custom medical mask 18 according to certain embodiments of method 10. In the embodiment shown, system 20 includes scanning system 22, processing system 26, and fabrication system 28. In particular embodiments, scanning system 22 may be coupled to processing system 26 through one or more data connections 30, allowing for data communication between scanning system 22 and processing system 26. Similarly, in certain embodiments, processing system 26 may be coupled to fabrication system 28 through the use of one or more data connections 32, allowing for data communication between processing system 26 and fabrication system 28. In certain embodiments, as shown in FIG. 2, processing system 26 and fabrication system 28 may be included in a combination system 24 that provides the functionality of both processing system 26 and fabrication system 28. In alternative embodiments, scanning system 22 and processing system 26 may be included within a combination system that provides the functionality of both scanning system 22 and processing system 26. In addition, in certain embodiments, the functionality of one or more of scanning system 22, processing system 26, and fabrication system 28 may each be distributed among multiple components.

Figure 3:
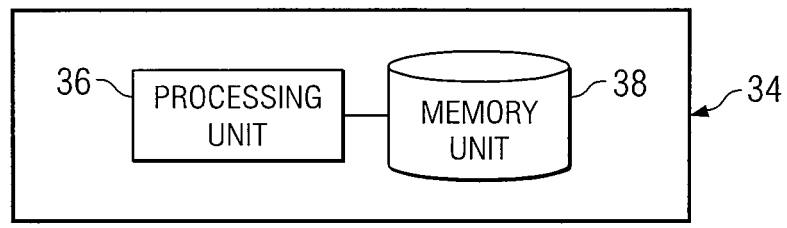
FIG. 3 illustrates an example module for use with an example processing system.

Each of scanning system 22, processing system 26, and fabrication system 28 may include one or more processing modules. FIG. 3 illustrates an example processing module 34 for use in system 20. Processing module 34 may include one or more processing units 36 coupled to one or more memory units 38 (which will be referred to as "processing unit 36" and "memory unit 38" throughout the remainder of this description). In certain embodiments, operations performed by processing module 34 are collectively performed by processing unit 36 and memory unit 38. Processing unit 36 may include any suitable microprocessor or microcontroller, according to particular needs. Memory unit 38 may take the form of volatile or nonvolatile memory including, without limitation, magnetic media, optical media, random access memory (RAM), read-only memory (ROM), removable media, or any other suitable data storage component.

Referring back to FIG. 2, scanning system 22 represents a system for collecting three-dimensional coordinate data for one or more surfaces of a physical object. Scanner 22 may utilize one or more of numerous well-known coordinate data collection techniques. In certain embodiments, scanning system 22 represents an optical scanner. In a particular embodiment, scanning system 22 represents a hand-held three-dimensional optical scanner, such as a HANDYSCAN 3D available from AGILE MANUFACTURING INC. of Ontario, Canada.

Processing system 26 represents an electronic system for use in performing one or more processes associated with data processing 14 on the three-dimensional coordinate data collected by scanning system 22. In certain embodiments, processing system 26 may represent a general purpose computer loaded with one or more software applications on a computer-readable medium. In a particular embodiment, these one or more software applications may include GEOMAGIC STUDIO available from RAINDROP GEOMAGIC, INC. of Research Triangle Park, N.C.

Fabrication system 28 represents a fully-automated or partially-automated system for forming a physical object from a three-dimensional electronic model. In certain embodiments, fabrication system 28 may represent a 3DP system, an SLS system, and/or an STL apparatus (SLA). In certain embodiments, an SLA operates by "building" parts one layer at a time. In certain embodiments, each layer may be formed by tracing a beam of light across the surface of a photo-reactive liquid, such as a photopolymer. In certain embodiments, the light may be focused on the surface of the photopolymer using one or more lasers each having a wavelength that is selected to interact with the photopolymer to cause the selective polymerization of the photopolymer wherever the laser is focused. In a particular embodiment, fabrication system 28 may be a VIPER SLA system, available from 3D SYSTEMS, INC. of Valencia, Calif. In a particular embodiment, the material used in fabrication system 28 to form custom medical mask 18 may include a photo-reactive epoxy resin, such as the FOTOTEC SL resin available from DREVE OTOPLASTIK, GmbH of Germany.

Data connections 30 and 32 each may represent one or more data connections providing for data communication between scanning system 22 and processing system 26 and between processing system 26 and fabrication system 28, respectively. Connections 30 and 32 may include wireline, wireless, and/or optical connections. In certain embodiments, one or more of connections 30 and 32 may represent a network such as a local area network (LAN), metropolitan area network (MAN), wide area network (WAN), global communications network such as the Internet, or any other suitable network. In certain embodiments, one or more of connections 30 and 32 may include a single network and/or multiple networks of the same type or different types to couple these components to one another, according to particular needs.

Figure 4A:
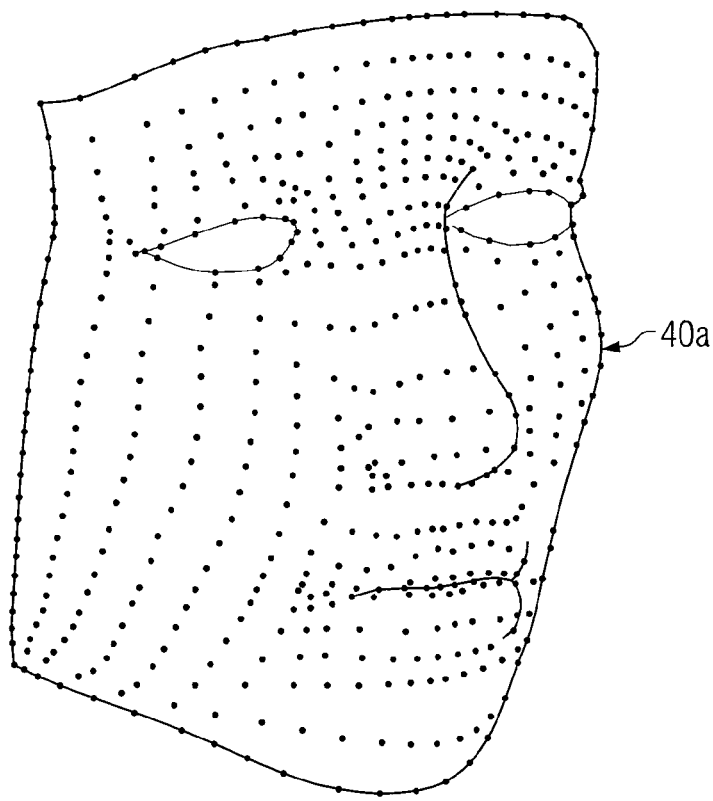

FIGS. 4A through 4E illustrate example electronic models 40 for use in forming a custom medical mask 18. In certain embodiments, one or more electronic models 40 may be stored in one or more memory units 38 within one or more processing modules 34 of system 20. FIG. 4A illustrates an example point-cloud model 40a that includes a cloud of three-dimensional coordinate data. Point-cloud model 40a represents an example of three-dimensional coordinate data that may be collected through data acquisition 12 and/or through the use of one or more scanning systems 22. For example, point-cloud model 40a may represent a collection of individual coordinate data points corresponding with electronic measurements of facial features of a particular user taken by one or more scanning systems 22. In certain embodiments, point cloud model 40a may represent multiple individual scans of a particular user's face, with each scan fitted or stitched together with other scans to form a single point-cloud model 40a. Point-cloud model 40a may be stored as a text file, as a comma delimited file, as a tab delimited file, and/or in any other appropriate electronic format.

Figure 4B:
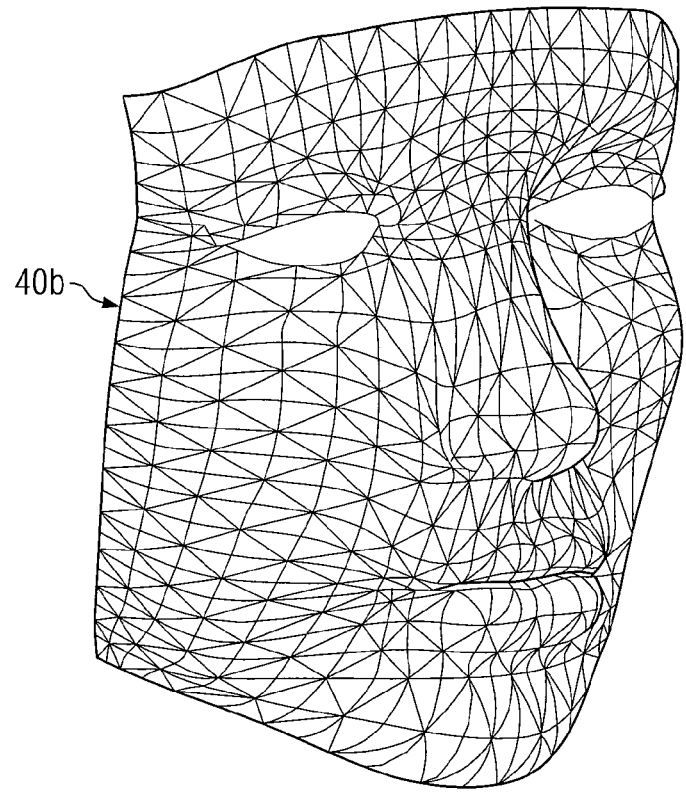

FIG. 4B illustrates an example polygon mesh model 40b that includes a plurality of polygons interconnected to form a mesh. In certain embodiments, polygon mesh model 40a may be formed from point-cloud model 40a through a process of selectively connecting adjacent pairs of coordinate data points from point-cloud model 40a. In certain embodiments, multiple polygons may be combined and/or merged together to reduce the total number of polygons included in polygon mesh model 40b. In the embodiment shown, each polygon included within polygon mesh model 40b is represented as a triangle. In alternative embodiments, any appropriate polygon or polygons may be used to form polygon mesh model 40b. Polygon mesh model 40b may be stored as a wire frame model, as a surface model, and/or in any other appropriate electronic format.

Figure 4C:
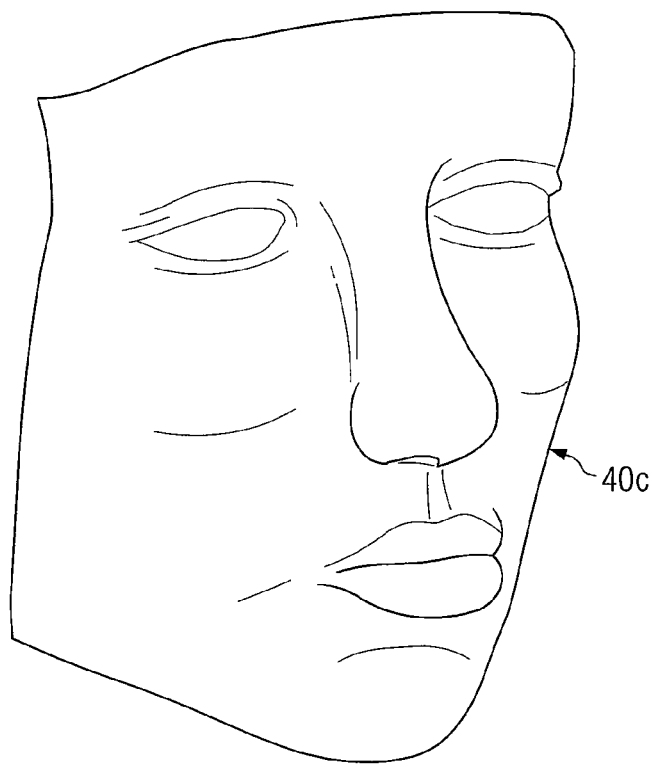

FIG. 4C illustrates an example NURBS model 40c. In certain embodiments, NURBS model 40c may represent one or more continuous surfaces mathematically approximating numerous polygons from polygon mesh model 40b. NURBS model 40c may be stored as an Initial Graphics Exchange Specification (IGES) model, as a Standard for the Exchange of Product Model Data (STEP) model, as an STL model, and/or in any other appropriate electronic format.

Figure 4D:
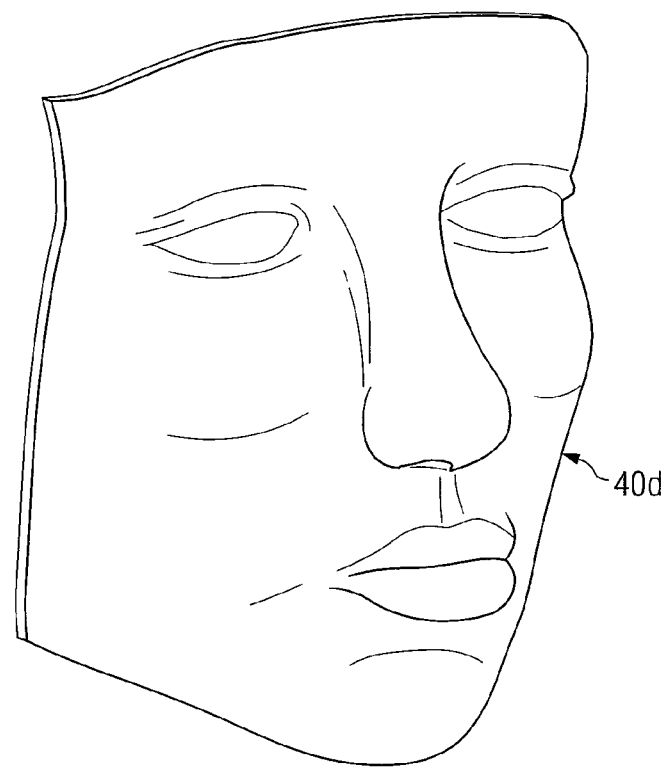

FIG. 4D illustrates an example solid model 40d. Solid model 40d may represent an electronic model created by extruding and/or offsetting one or more surfaces from NURBS model 40c and/or polygon mesh model 40b. Solid model 40d may be stored as an IGES model, as a STEP model, as an STL model, and/or in any other appropriate electronic format.

Figure 4E:
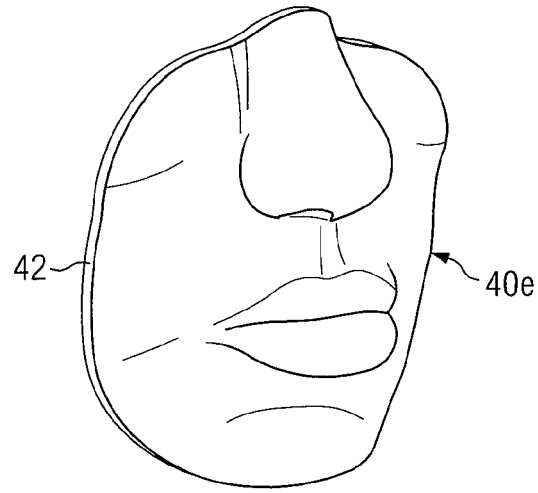

FIG. 4E illustrates an example trimmed model 40e. Trimmed model 40e may represent a trimmed version of solid model 40d with one or more surfaces limited by one or more trim surfaces 42. Trimmed model 40e may be stored as an IGES model, as a STEP model, as an STL model, and/or in any other appropriate electronic format.

In operation, according to particular embodiments, scanning system 22 may collect coordinate data from the facial features of a particular user. This coordinate data may be utilized to generate point-cloud model 40a according to data acquisition 12. In certain embodiments, point-cloud model 40a may be communicated via connection 30 or otherwise to processing system 26. Processing system 26 may perform one or more processing steps to manipulate and/or modify the data collected by scanning system 22, according to data processing 14. For example, the data collected by scanning system 22 may be converted from point-cloud model 40a to one or more of polygon mesh model 40b and NURBS model 40c. In certain embodiments, one or more of polygon mesh model 40b and NURBS model 40c may be offset and/or extruded to form solid model 40d. The thickness of the offset and/or extrusion may correspond to a selected thickness for custom medical mask 18. For example, in certain embodiments, the offset and/or extrusion thickness of solid model 40d may be in the range between 0.05 and 0.20 inches. In a particular embodiment, the offset and/or extrusion thickness of solid model 40d may be 0.125 inches. In certain embodiments, the offset and/or extrusion thickness of solid model 40d may vary and may be different for different portions of solid model 40d.

In certain embodiments, solid model 40d may be trimmed to selectively adjust and/or define a periphery of solid model 40d using one or more trim surfaces 42 to create trimmed model 40e. In certain embodiments, the one or more trim surfaces 42 may be generated and/or utilized to define a periphery to correspond with a selected shape for custom medical mask 18. For example, in a particular embodiment, one or more trim surfaces 42 may be generated and/or utilized to define a periphery around a region corresponding to the particular user's mouth and portions of the particular user's nose. In certain embodiments, the step of trimming one or more surfaces to define a periphery may be performed with one or more of point-cloud model 40a, polygon mesh model 40b, NURBS model 40c, and/or solid model 40d. In certain embodiments, trimmed model 40e may be communicated via connection 32 or otherwise to fabrication system 28. Fabrication system 28 may perform one or more steps to form custom medical mask 18 from trimmed model 40e.

Figure 5:
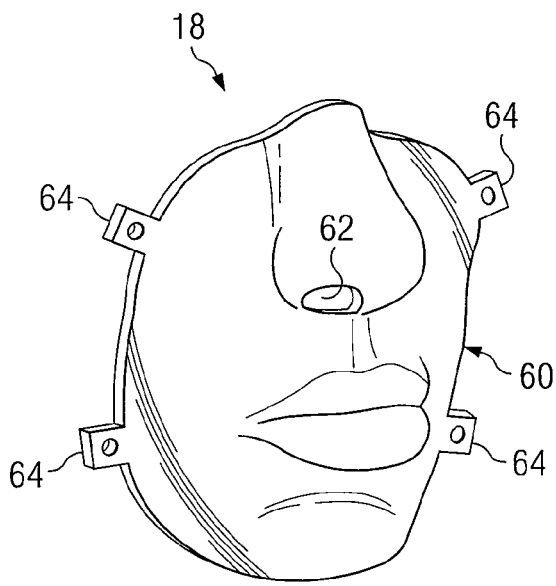

FIG. 5 illustrates an example custom medical mask 18 that may be formed, at least in part, by fabrication system 28. As shown, custom medical mask 18 may include body 60, one or more openings 62, and/or one or more tabs 64. Body 60 may represent one or more pieces of thin material configured to cover the particular user's nose and/or mouth. The one or more pieces of thin material may be shaped to correspond to the unique facial features of the particular user. The one or more pieces of thin material may include a polymerized photopolymer material. The one or more openings 62 may allow for access through body 60 to the particular user's nostrils and/or mouth, when custom medical mask 18 is positioned over the particular user's face. Tab 64 may operate to couple custom medical mask 18 to one or more straps and/or other devices to couple custom medical mask 18 to the particular user. One or more of openings 62 and/or tabs 64 may be integrally formed with body 60 when custom medical mask 18 is formed with fabrication system 28. In these embodiments, electronic model 40 used with fabrication system 28 to form custom medical mask 18 may include model elements corresponding to the one or more openings 62 and/or tabs 64. In alternative embodiments, one or more of openings 62 and/or tabs 64 may be added to body 60 after custom medical mask 18 is formed with fabrication system 28. For example, one or more openings 62 may be cut, drilled, and/or pressed out of body 60 after body 60 has been formed. Similarly, one or more tabs 64 may be coupled to body 60 through the use of an adhesive or any other appropriate coupling technique.

In certain embodiments, the periphery of custom medical mask 18 may be defined by trim surface 42 in trimmed model 40e prior to forming custom medical mask 18 with fabrication system 28. In certain embodiments, the periphery of custom medical mask 18 may be further modified and/or trimmed to achieve an improved fit and/or desired shape for custom medical mask 18 after custom medical mask 18 is formed by fabrication system 28.

Figure 6A:
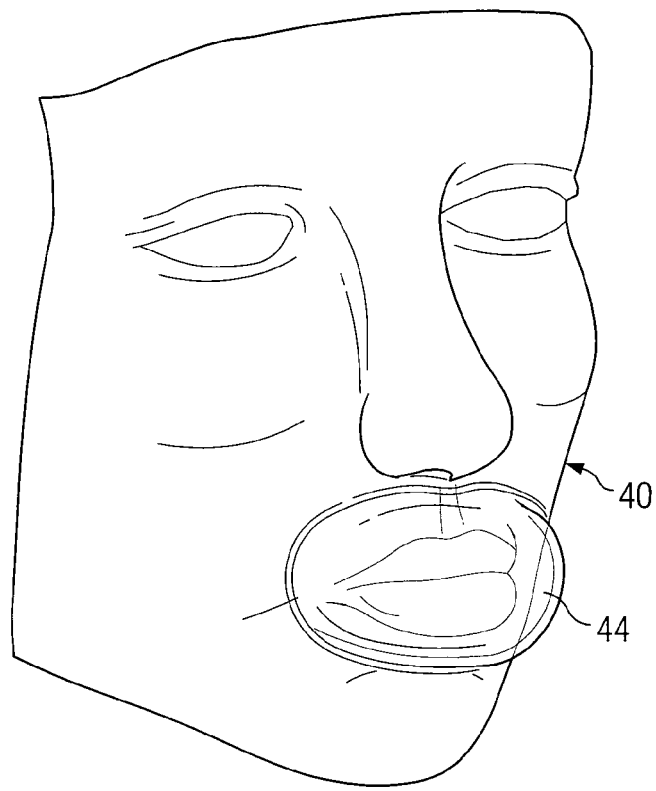
FIGS. 6A and 6B illustrate example electronic models for use in forming a custom medical mask with an oral chamber.
Figure 6B:
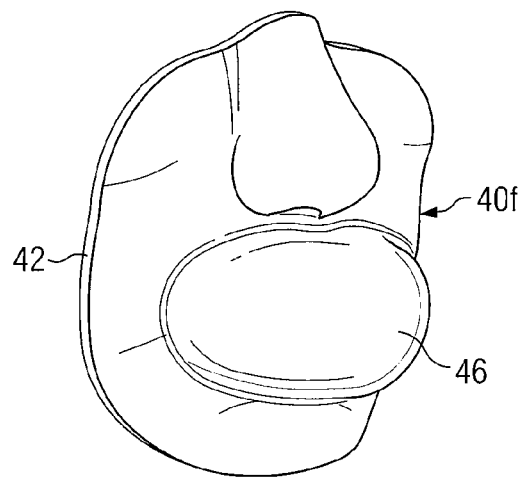

FIGS. 6A and 6B illustrate example electronic models 40 for use in forming a custom medical mask 18 with an oral chamber. In certain embodiments, it may be advantageous to form a custom medical mask 18 having a chamber substantially surrounding the mouth or lips of a particular user. Such a chamber may be advantageous to allow the mouth and/or lips of the particular user to move while the particular user is wearing custom medical mask 18. In certain embodiments, electronic model 40 for use in forming custom medical mask 18 having an oral chamber may be generated through the use of chamber model 44. Chamber model 44 may represent an electronic surface and/or solid model corresponding to a selected shape for an oral chamber for custom medical mask 18. In certain embodiments, chamber model 44 may be combined, overlaid, and/or merged with electronic model 40. In certain embodiments, once chamber model 44 has been combined, overlaid, and/or merged with electronic model 40, a trimmed model 40f may be developed such that at least a portion of trimmed model 40f in region 46 does not directly correspond to the facial features of the particular user.

In an alternative embodiment, rather than using chamber model 44 to generate trimmed model 40f, a physical mold or other structure may be placed on the face of the particular user at the time of data acquisition 12. In these embodiments, the three-dimensional coordinate data collected for the particular user's face may also include three-dimensional coordinate data of the mold or structure. This three-dimensional coordinate data may then be used to generate trimmed model 40f such that at least a portion of trimmed model 40f in region 46 does not directly correspond to the facial features of the particular user.

Figure 7:
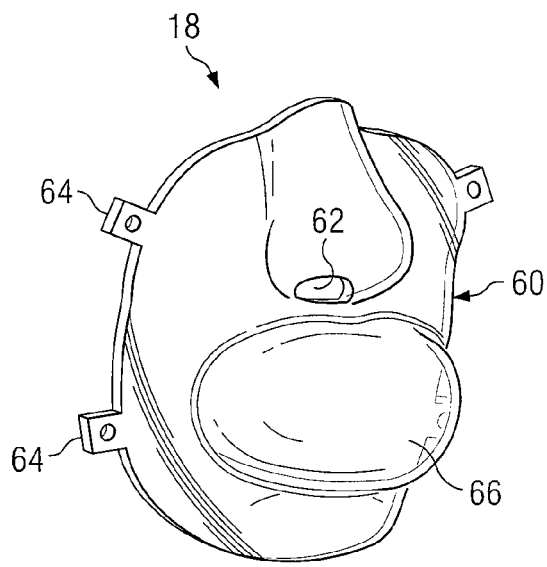

FIG. 7 illustrates an example custom medical mask 18, with oral chamber 66, that may be formed, at least in part, by fabrication system 28. As shown, in addition to the features described above in relation to FIG. 5, custom medical mask 18 may include oral chamber 66. Oral chamber 66 may represent a region of body 60 corresponding with an area around the mouth or lips of the particular user that is configured to be offset from the lips or mouth of the particular user when custom medical mask 18 is positioned on the particular user's face. In certain embodiments, custom medical mask 18 may be formed with fabrication system 28 using trimmed model 40f. In certain embodiments, custom medical mask 18 with oral chamber 66 may allow the particular user to move their mouth and/or lips while custom medical mask 18 is positioned on the particular user's face.

Figure 8A:
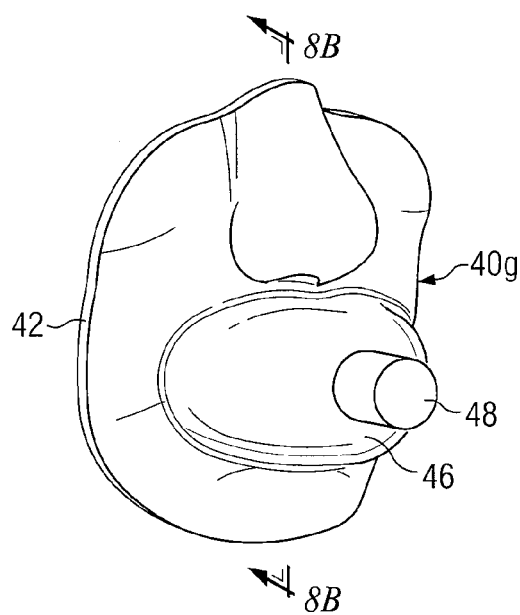
FIGS. 8A and 8B illustrate example electronic models for use in forming a custom medical mask with a receptacle for a coupling device.
Figure 8B:
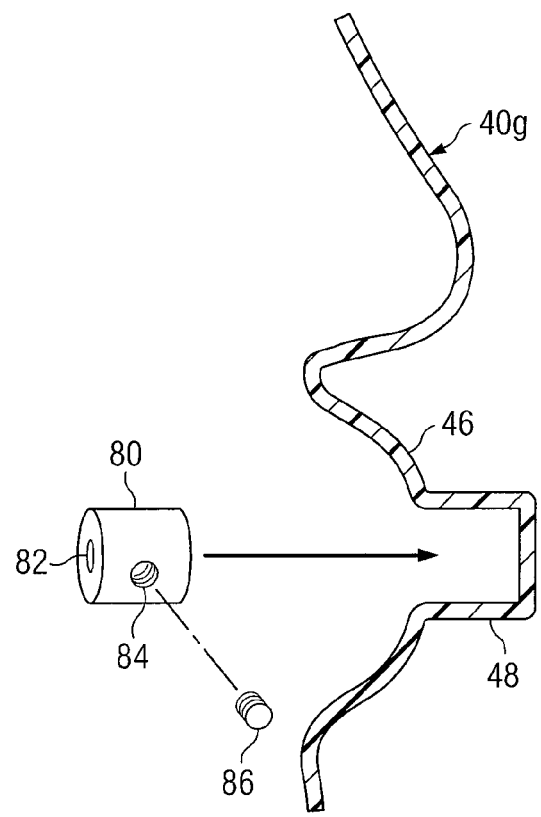

FIGS. 8A and 8B illustrate example electronic models 40 for use in forming a custom medical mask 18 with a receptacle for a coupling device. In certain embodiments, it may be advantageous to form a custom medical mask 18 configured for use with a coupling device 80. Coupling device 80 may represent one or more structures configured to couple custom medical mask 18 to an oral appliance. In a particular embodiment, coupling device 80 may represent a sleeve with an opening 82 configured to receive a post and/or other structure of an oral appliance. In particular embodiments, coupling device 80 may further include one or more openings 84 configured to receive a threaded set screw 86 to retain a post and/or other structure of an oral appliance within coupling device 80. In certain embodiments, an electronic model 40 for use in forming a custom medical mask having a receptacle for a coupling device may be generated through the use of receptacle model 48. Receptacle model 48 may represent an electronic surface and/or solid model corresponding to a selected shape for a receptacle for coupling device 80. In a particular embodiment, receptacle model 48 may represent an electronic surface and/or solid model shaped to substantially surround the outer dimensions of coupling device 80. In certain embodiments, receptacle model 48 may be combined, overlaid, and/or merged with electronic model 40. In certain embodiments, once receptacle model 48 has been combined, overlaid, and/or merged with electronic model 40, a trimmed model 40g may be developed for use in forming a custom medical mask 18 with a receptacle for coupling device 80.

In an alternative embodiment, rather than using receptacle model 44 to generate trimmed model 40g, a coupling device 80 may be positioned on or near the face of the particular user at the time of data acquisition 12. In these embodiments, the three-dimensional coordinate data collected for the particular user's face may also include three-dimensional coordinate data of coupling device 80. This three-dimensional coordinate data may then be used to generate trimmed model 40g such that trimmed model 40g includes a region shaped to substantially surround the outer dimensions of coupling device 80. Similarly, in certain embodiments, the three-dimensional coordinate data collected for the particular user's face may also include three-dimensional coordinate data of a portion of an oral appliance. In embodiments in which the collected three-dimensional coordinate data includes three-dimensional coordinate data of a portion of an oral appliance, the data may be used to form a custom medical mask that is custom oriented to the oral appliance based on this collected data. In a particular embodiment, coupling device 80 may be precisely positioned relative to the teeth and unique facial features of the particular user at the time of data acquisition 12, such that custom medical mask 18 formed using the data collected in data acquisition 12 may be custom oriented to the particular user's teeth and unique facial features. For example, an oral appliance with a post may be positioned within the particular user's mouth and coupling device 80 may be coupled to a post of the oral appliance positioned within the particular user's mouth at the time of data acquisition 12. An oral appliance positioned within the particular user's mouth may include a bite register, a wax mold, an upper arch, and/or a lower arch.

Figure 9:
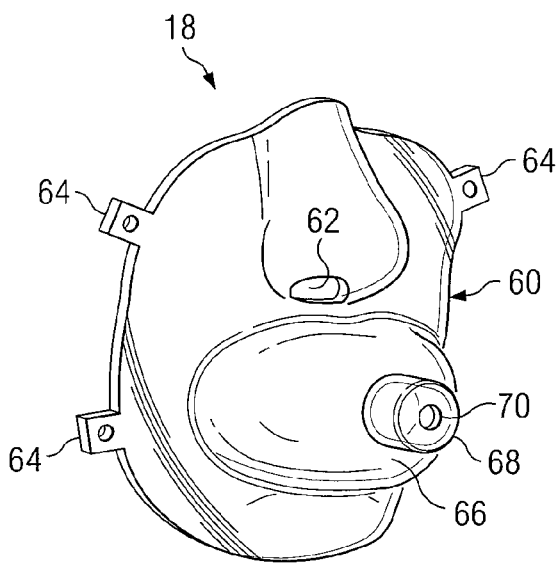
FIG. 9 illustrates an example custom medical mask with a receptacle for a coupling device.

FIG. 9 illustrates an example custom medical mask 18 with receptacle 68 for a coupling device 80. Custom medical mask 18 with receptacle 68 may be formed, at least in part, by fabrication system 28. As shown, in addition to the features described above in relation to FIGS. 5 and 7, custom medical mask 18 may include receptacle 68 configured to receive coupling device 80. Receptacle 68 may represent a sleeve or enclosure in body 60 shaped to receive and/or support coupling device 80. As shown, receptacle 68 may include opening 70. Opening 70 may be configured to allow access through body 60 for another structure, such as a post of an oral appliance. One or more of receptacle 68 and/or opening 70 may be integrally formed with body 60 when custom medical mask 18 is formed with fabrication system 28. In these embodiments, electronic model 40 used with fabrication system 28 to form custom medical mask 18 may include model elements corresponding to the one or more of receptacle 68 and/or opening 70. For example, custom medical mask 18 may be formed with fabrication system 28 using trimmed model 40g. In alternative embodiments, one or more of receptacle 68 and/or opening 70 may be added to body 60 after custom medical mask 18 is formed with fabrication system 28. For example, opening 70 may be cut, drilled, and/or pressed out of body 60 after body 60 has been formed. In certain embodiments, custom medical mask 18 with receptacle 68 may cooperate with coupling device 80 to couple custom medical device 18 to an oral appliance to improve the positioning and/or fit of custom medical mask 18 for the particular user.

Figure 10:
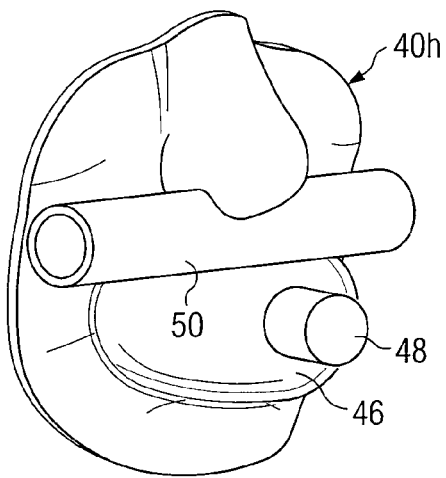
FIG. 10 illustrates an example electronic model for use in forming a custom medical mask with a fitting for a clinical gas delivery system.

FIG. 10 illustrates an example electronic model for use in forming a custom medical mask 18 with a fitting for a clinical gas delivery system. In certain embodiments, it may be advantageous for custom medical mask 18 to couple to a suitable clinical gas delivery system. A suitable clinical gas delivery system may be a Continuous Positive Airway Pressure (CPAP) system, a Bilevel Positive Airway Pressure (Bi-PAP) system, and/or a system configured to deliver an anesthetic, oxygen, and/or other appropriate clinical gases to a particular user wearing custom medical mask 18. In certain embodiments, an electronic model 40 for use in forming a custom medical mask having a fitting for a clinical gas delivery system may be generated through the use of fitting model 50. In certain embodiments, fitting model 50 may be combined, overlaid, and/or merged with electronic model 40 to generate trimmed model 40h. Fitting model 50 may represent an electronic replica of a fitting configured to couple custom medical mask 18 to a clinical gas delivery system. In certain embodiments, once fitting model 50 has been combined, overlaid, and/or merged with electronic model 40, a trimmed model 40h may be developed for use in forming a custom medical mask 18 with a fitting for a clinical gas delivery system.

Figure 11:
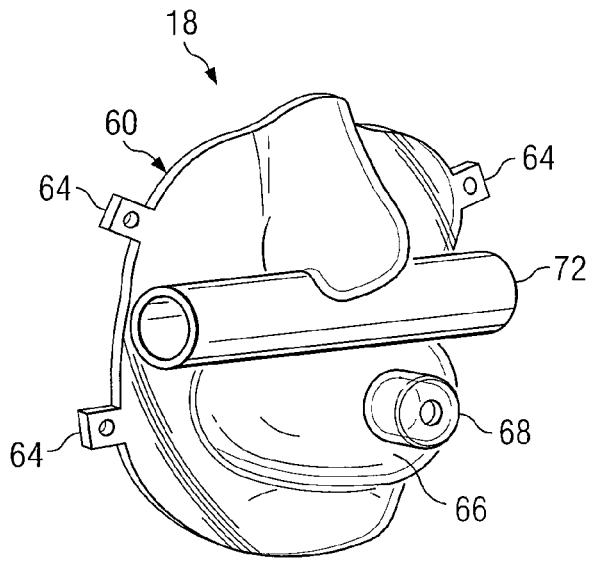
FIG. 11 illustrates an example custom medical mask with a fitting for a clinical gas delivery system.

FIG. 11 illustrates an example custom medical mask 18 with fitting 72 for a clinical gas delivery system. Custom medical mask 18 with fitting 72 may be formed, at least in part, by fabrication system 28. As shown, in addition to the features described above in relation to FIGS. 5, 7, and 9, custom medical mask 18 may include fitting 72 configured to couple to a clinical gas delivery system such as a CPAP system or a BiPAP system. Fitting 72 may represent a structure configured to deliver a flow of gas from one or more hoses and/or tubes through an opening in body 60. In a particular embodiment, fitting 72 may represent a tube positioned to deliver a flow of gas to one or more nostrils of the particular user when the custom medical mask is positioned on the particular user's face. Fitting 72 may be integrally formed with body 60 when custom medical mask 18 is formed with fabrication system 28. In these embodiments, electronic model 40 used with fabrication system 28 to form custom medical mask 18 may include model elements corresponding to fitting 72. For example, custom medical mask 18 may be formed with fabrication system 28 using trimmed model 40h. In alternative embodiments, fitting 72 may be added to body 60 after custom medical mask 18 is formed with fabrication system 28. For example, fitting 72 may be coupled to body 60 through the use of an adhesive or any other appropriate coupling technique. In certain embodiments, custom medical mask 18 with fitting 72 may cooperate with a clinical gas delivery system to deliver a clinical gas, such as anesthetic, oxygen, and/or air, to the particular user when the custom medical mask is positioned on the particular user's face.

Although the present invention has been described in several embodiments, a plenitude of changes, substitutions, variations, transformations, and modifications may be suggested to one skilled in the art, and it is intended that the present invention encompass such changes, substitutions, variations, transformations, and modifications as fall within the scope of the appended claims.

What is claimed is:

1. A custom medical mask formed for a particular user from a three-dimensional electronic model, comprising:
   a body formed from a polymerized photopolymer material;
   an interior surface of the body configured to seat on the particular user's face and comprising a physical embodiment of a three-dimensional electronic model corresponding to unique facial features of the particular user;
   a fitting configured to couple to a clinical gas delivery system, wherein the fitting and the body form one integral piece of the polymerized photopolymer material; and
   at least one selected from the group consisting of:
   an oral chamber shaped to be offset from the mouth of the particular user when the custom medical mask is positioned on the particular user's face; and
   a coupling device shaped to couple the custom medical mask to an oral appliance;
   wherein the three-dimensional electronic model was merged with an electronic fitting model and at least one of an oral chamber model representing an oral chamber and a fitting model representing a coupling device.

2. The custom medical mask of claim 1, wherein the photopolymer material comprises a photo-reactive epoxy resin.

3. The custom medical mask of claim 1, further comprising an exterior surface of the body offset from the interior surface a distance between 0.05 and 0.20 inches.

4. A method of creating a three-dimensional electronic model for use in forming a custom medical mask for a particular user, comprising:
   scanning at least a portion of the particular user's face using an electronic scanning device;
   generating a three-dimensional electronic model of the portion of the particular user's face based on the scanning;
   transmitting the three-dimensional electronic model of the portion of the particular user's face for use in forming the custom medical mask for the particular user from a photopolymer using a stereolithography apparatus;
   processing the three-dimensional electronic model of the portion of the particular user's face to create a stereolithography model for use in forming the custom medical mask from the photopolymer using the stereolithography apparatus;
   wherein the processing comprises:
      merging the three-dimensional electronic model with an electronic fitting model representing a fitting shaped to couple to a clinical gas delivery system; and
      merging the three-dimensional electronic model with an electronic model selected from the group consisting of:
         an oral chamber model representing an oral chamber shaped to be offset from the mouth of the particular user when the custom medical mask is positioned on the particular user's face; and
         a receptacle model representing a coupling device shaped to couple the custom medical mask to an oral appliance.

5. The method of claim 4, wherein the photopolymer comprises a photo-reactive epoxy resin.

6. The method of claim 4, wherein processing the three-dimensional electronic model to create the stereolithography model comprises extruding a surface of the three-dimensional electronic model in a direction normal to the surface a distance between 0.05 and 0.20 inches.

7. The method of claim 4, further comprising focusing a light source on the photopolymer material in a pattern corresponding to the stereolithography model to polymerize the photopolymer material to form the custom medical mask from the photopolymer.

8. A system for forming a custom medical mask for a particular user from a three-dimensional electronic model, comprising:
   a photopolymer material;
   a three-dimensional electronic model of a custom medical mask, the three-dimensional electronic model comprising:
      a first surface that corresponds to unique facial features of the particular user;
      an electronic model of a fitting configured to couple to a clinical gas delivery system; and
      an electronic model selected from the group consisting of:
         an oral chamber model representing an oral chamber shaped to be offset from the mouth of the particular user when the custom medical mask is positioned on the particular user's face; and
         a receptacle model representing a coupling device shaped to couple the custom medical mask to an oral appliance;
   wherein the electronic model of the fitting and the selected electronic model have been merged with the first surface; and
   a stereolithography apparatus operable to focus a light source on the photopolymer material in a pattern corresponding to the three-dimensional electronic model to polymerize the photopolymer material to form the custom medical mask for the particular user with a fitting configured to couple to the clinical gas delivery system.

9. The system of claim 8, wherein the photopolymer material comprises a photo-reactive epoxy resin.

10. The system of claim 8, wherein the three-dimensional electronic model further comprises a second surface offset from the first surface a distance between 0.05 and 0.20 inches.

11. A computer-implemented system for use in connection with forming a custom medical mask for a particular user from a three-dimensional electronic model, comprising:
   one or more memory units storing a three-dimensional electronic model of a custom medical mask, the three-dimensional electronic model suited for use with a stereolithography apparatus and comprising a first surface that corresponds to unique facial features of the particular user; and
   one or more processing units coupled to the one or more memory units and operable to access the three-dimensional electronic model in the one or more memory units for use in connection with forming a custom medical mask for a particular user using the SLA; and
   wherein the three-dimensional electronic model further comprises:
      a model of a fitting configured to couple to a clinical gas delivery system; and
      a model selected from the group consisting of:
         an oral chamber model representing an oral chamber shaped to be offset from the mouth of the particular user when the custom medical mask is positioned on the particular user's face; and
         a receptacle model representing a coupling device shaped to couple the custom medical mask to an oral appliance; and
   wherein the electronic model of the fitting and the selected electronic model have been merged with the first surface.

12. The system of claim 11, wherein the three-dimensional electronic model further comprises a second surface offset from the first surface a distance between 0.05 and 0.20 inches.

13. The system of claim 11, wherein the one or more processing units are operable to access the three-dimensional electronic model over a network.

14. A method of creating a three-dimensional electronic model for use in forming a custom medical mask for a particular user, comprising:
   receiving a three-dimensional electronic model of at least a portion of the particular user's face; and
   processing the three-dimensional electronic model of the portion of the particular user's face to create a stereolithography model that is suited for use with a stereolithography apparatus in creating the custom medical mask for the particular user, the stereolithography model comprising a first surface corresponding to unique features of the portion of the particular user's face;
   wherein the processing comprises:
      merging the three-dimensional electronic model with an electronic representation of a fitting configured to couple to a clinical gas delivery system; and
      merging the three-dimensional electronic model with at least one selected from the group consisting of:
         an electronic representation of an oral chamber shaped to be offset from the mouth of the particular user when the custom medical mask is positioned on the particular user's face; and
         an electronic representation of a coupling device shaped to couple the custom medical mask to an oral appliance.

15. The method of claim 14, wherein the stereolithography model further comprises a second surface offset from the first surface in a direction normal to the first surface a distance between 0.05 and 0.20 inches.

16. A method of creating a three-dimensional electronic model for use in forming a custom-fit medical mask, comprising:
   scanning at least a portion of a human face using an electronic scanning device;
   based at least in part on the scanning, generating a three-dimensional electronic model of the portion of the human face;
   merging the three-dimensional electronic model with a fitting model representing a fitting shaped to couple to a clinical gas delivery systems;
   merging the three-dimensional electronic model with an electronic model selected from the group consisting of:
   an oral chamber model representing an oral chamber shaped to be offset from the mouth of the particular user when the custom medical mask is positioned on the particular user's face; and
   a receptacle model representing a coupling device shaped to couple the custom medical mask to an oral appliance; and
   transmitting the merged three-dimensional electronic model to one or more processing modules adapted to create an electronic stereolithography model by processing the transmitted three-dimensional model, the electronic stereolithography model readable by a stereolithography apparatus adapted to form the custom-fit medical mask from a photopolymer using the electronic stereolithography model.

17. A method of creating an electronic stereolithography model for use in forming a custom-fit medical mask, comprising:

scanning at least a portion of a human face using an electronic scanning device;

based at least in part on the scanning, generating a three-dimensional electronic model of the portion of the human face;

merging the three-dimensional electronic model with an electronic model of a fitting configured to couple to a clinical gas delivery system; and merging the three-dimensional electronic model with an electronic model selected from the group consisting of:
- an oral chamber model representing an oral chamber shaped to be offset from the mouth of a user when a custom-fit medical mask is positioned on the user's face; and
- a receptacle model representing a coupling device shaped to couple a custom-fit medical mask to an oral appliance;

wherein the electronic stereolithography model is readable by a stereolithography apparatus adapted to form a custom-fit medical mask using the electronic stereolithography model, the custom-fit medical mask comprising the fitting configured to couple to the clinical gas delivery system and at least one of an oral chamber shaped to be offset from the mouth of a user when the custom-fit medical mask is positioned on the user's face and a coupling device shaped to couple a custom-fit medical mask to an oral appliance.

\* \* \* \* \*